United States Patent
Farge et al.

(10) Patent No.: US 9,435,789 B2
(45) Date of Patent: Sep. 6, 2016

(54) ARTICLE FOR BIOLOGICAL ANALYSIS

(75) Inventors: Agathe Farge, Rive de Gier (FR); Denis Januel, Lyons (FR)

(73) Assignee: BIOMERIEUX, Marcy l'etoile (FR)

( * ) Notice: Subject to any disclaimer, the term of this patent is extended or adjusted under 35 U.S.C. 154(b) by 238 days.

(21) Appl. No.: 13/881,873

(22) PCT Filed: Nov. 22, 2011

(86) PCT No.: PCT/FR2011/052727
§ 371 (c)(1),
(2), (4) Date: Apr. 26, 2013

(87) PCT Pub. No.: WO2012/069758
PCT Pub. Date: May 31, 2012

(65) Prior Publication Data
US 2013/0217142 A1    Aug. 22, 2013

(30) Foreign Application Priority Data

Nov. 25, 2010 (FR) ...................................... 1059712

(51) Int. Cl.
| | |
|---|---|
| *G01N 21/00* | (2006.01) |
| *G01N 33/50* | (2006.01) |
| *B65D 75/32* | (2006.01) |
| *B65D 81/26* | (2006.01) |
| *G01N 33/487* | (2006.01) |

(52) U.S. Cl.
CPC ............. *G01N 33/50* (2013.01); *B65D 75/326* (2013.01); *B65D 81/267* (2013.01); *G01N 33/48778* (2013.01); *B65D 2575/3254* (2013.01)

(58) Field of Classification Search
None
See application file for complete search history.

(56) References Cited

U.S. PATENT DOCUMENTS

| | | |
|---|---|---|
| 3,036,700 A | 5/1962 | Krug |
| 3,540,579 A | 11/1970 | Hellstrom |
| 4,150,744 A | 4/1979 | Fennimore |
| 4,739,881 A | 4/1988 | Bruso |
| 5,962,333 A | 10/1999 | Incorvia et al. |

FOREIGN PATENT DOCUMENTS

| | | |
|---|---|---|
| EP | 1 754 971 A1 | 2/2007 |
| EP | 1 803 659 A1 | 7/2007 |
| WO | WO 00/63288 A1 | 10/2000 |

OTHER PUBLICATIONS

Mar. 6, 2012 International Search Report Issued in International Patent Application No. PCT/FR2011/052727 (with translation.).
Mar. 6, 2012 Written Opinion of the International Searching Authority issued in International Patent Application No. PCT/FR2011/052727 (with translation).

*Primary Examiner* — Robert Xu
(74) *Attorney, Agent, or Firm* — Oliff PLC

(57) ABSTRACT

The present invention generally relates to the field of analysis, for example biological analysis. More specifically, the present invention relates to an article, especially for biological analysis, the article including: a first sheet, a second sheet, superimposed on the first sheet, the first and second sheets being joined on all of their sides in order to form a sealed package, at least one analysis device, placed inside the package, a rigid desiccation device, also constituting a device perforating the first or second sheet of the package, in order to access the analysis device, and one of the first and second sheets contains a notch which constitutes a preferential folding area.

17 Claims, 2 Drawing Sheets

ARTICLE FOR BIOLOGICAL ANALYSIS

The present invention generally relates to the field of analysis, for example biological analysis. More specifically, the present invention relates to a package for an analysis device.

In the field of analysis, in particular that of biological analysis, it is common practice to use single-use sterile devices packaged in individual packages. This is the case for example for blood sampling devices, such as syringes or needles, surface-sampling devices such as swabs, and culture media seeding devices, such as disposable oeses. It is also common practice to find reagents packaged in single-use packages.

Most of the time, the packages for these devices are made up of two plastic films sealed to one another around their perimeter, with one of the two being generally transparent. One of the two films can also be a metal film, such as an aluminium film or a multilayer film made up for example of an aluminium layer and of a plastic layer.

This type of package can be opened in different ways. The first consists in separating the two films which make up the package. To this end, an area at which the two films are not sealed, generally in a corner, allows each of these to be gripped in order to separate them. The handling of this type of package is not always very easy. Indeed, the step of separating the two films can sometimes be tricky as a result of the difficulty of gripping the two films. The use of protective gloves by the handler makes this step even trickier. Furthermore, once the two films have detached, the analysis device may slide out of the package and fall. It then becomes unusable.

A second way of opening the package consists in using the analysis device, when this is rigid, to pierce one of the two films which make up the package. It is evident that at least one of the films must have a limited breaking resistance to allow the analysis device to pierce it. To this end, the device is pressed against one of the two films of the package. Such a package is, for example, described in document U.S. Pat. No. 3,036,700. Preferably, the film described in this document and intended to be pierced includes a weakened area to facilitate piercing. Such an opening means requires that the analysis device be a device which is rigid and sufficiently robust to withstand the stress.

A third way of opening the package consists in placing a blunt object inside the package, said object enabling the piercing of one of the two films which make up the package. Such a package is for example described in document U.S. Pat. No. 4,739,881. The main problem constituted by such an assembly is the risk incurred by the handler when opening the package. Indeed, the handler can easily injure himself/herself with the blunt object when the latter pierces the package.

In view of the technical problems raised by the state of the art considered above, one of the essential objectives of the present invention is to provide an article especially for biological analysis, including a package and an analysis device inside, allowing simple opening of the package, whether the analysis device is rigid or flexible; such opening being able to be performed with one hand.

Another objective of the present invention is to provide an article especially for biological analysis, the opening of the packaging of which does not entail a risk of injuring the handler.

Another objective of the present invention is an article especially for biological analysis which allows easy gripping of the analysis device, once the package is opened.

These objectives amongst others are resolved by the present invention, which primarily relates to an article, especially for biological analysis, said article comprising:
  a first sheet,
  a second sheet, superimposed on said first sheet, said first and second sheets being joined on all of their sides in order to form a sealed package,
  at least one analysis device, placed inside said sealed package;
  a rigid desiccation means,
wherein the desiccation means also constitutes a means of perforating the first or second layer of said package, in order to access the analysis device.

In an advantageous embodiment of the article according to the invention, the desiccation means is a solid polymer material containing a desiccant.

Preferably, the desiccation means is substantially rectangular parallelepiped in shape. Such a shape is particularly suitable for optimising the perforation of the package.

According to a particular embodiment, one of said first and second sheets includes a preferential folding area.

According to another particular embodiment, one of said first and second sheets includes an analysis device gripping area.

The biological analysis device contained in the package can advantageously be a reaction strip.

Preferably, the reaction strip bears antibiotics in the form of a concentration gradient.

According to another particular embodiment, at least one of said first and second sheets comprises an aluminium layer.

Advantageously, one of said first and second sheets comprises an aluminium-polymer composite laminate.

Another object of the present invention relates to the use of an article according to the invention for biological analysis.

The aims and advantages of the present invention will be better understood in light of the following detailed description, which is given with reference to the drawings in which.

Figure 1:
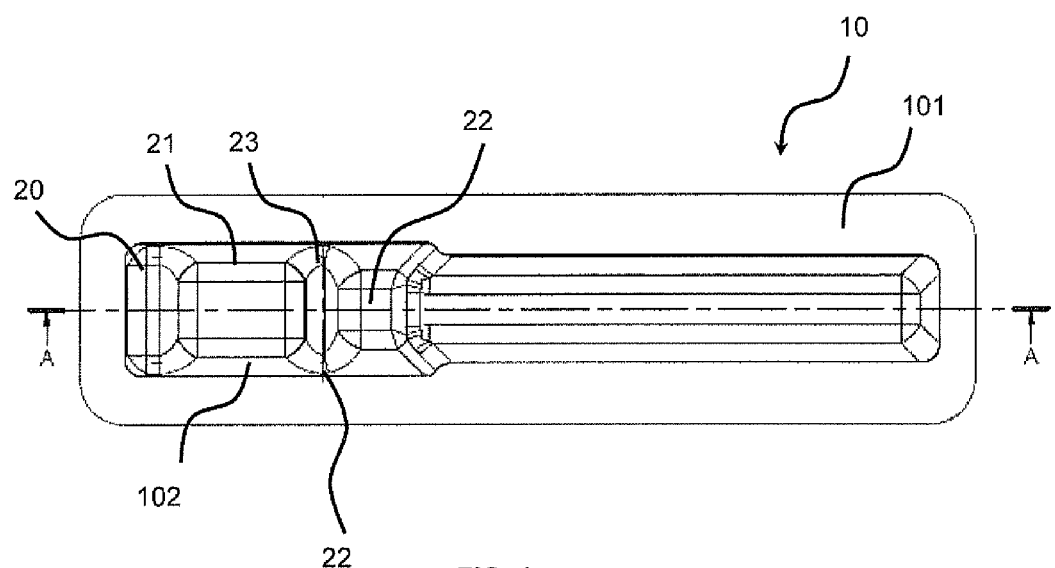
FIG. 1 shows a top view of an article for biological analysis according to the invention.
Figure 2:
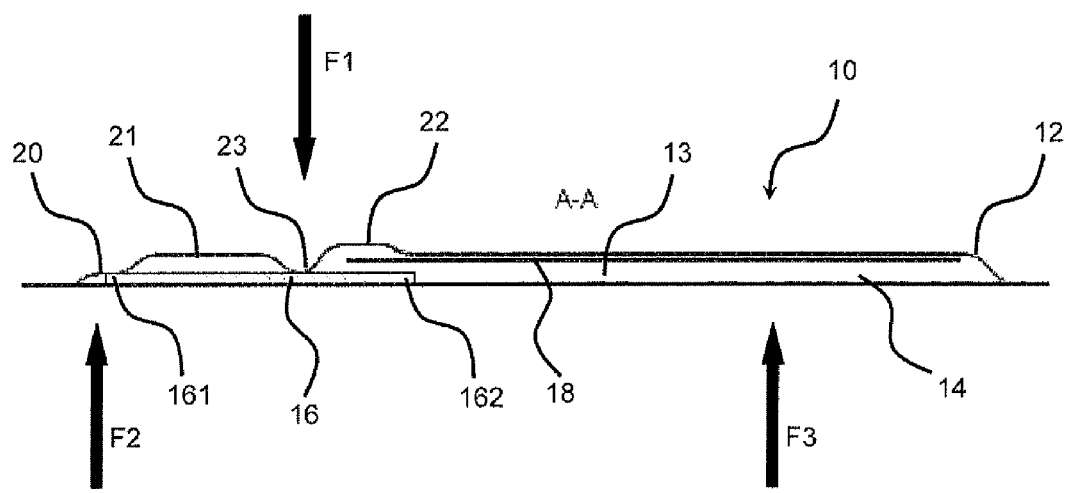
FIG. 2 shows a longitudinal cross-section view along axis A-A of the article for biological analysis shown in FIG. 1.

The article 10 according to the invention is shown in top view in FIG. 1. This article has a substantially rectangular general shape, with a substantially flat part 101 and a substantially bulging part 102. As can be seen in FIG. 2, which shows a cross-section of article 10 shown in FIG. 1, the flat part 101 in fact constitutes a peripheral area at which the first sheet 12 and the second sheet 14 constituting the package are joined. The sheets 12 and 14 are joined by thermosealing. For its part, the bulging part 102 defines the inner cavity 13 of the package. It appears clearly in FIG. 2 that this bulging part 102 is essentially constituted by a moulding of the first sheet 12, which is the upper sheet in this FIG. 2. To this end, the first sheet 12 is preferably constituted of a flexible water-impermeable material. Such a film may be an aluminium-plastic composite laminate (oriented polyamide (oPA), Polyvinyl chloride (PVC)), having the ability to be cold formed and with a minimal breaking resistance. Such films are well known and largely used in packaging in particular of medications, commonly referred to as blister packaging. Films marketed by the company AMCOR under the FORMPACK® mark may be cited by way of example.

The sheet 14, which is the lower sheet in FIG. 2 is, for its part, substantially flat. It is a capping sealing sheet. It must furthermore have low breaking resistance properties. Indeed, this sheet is intended to be pierced to make it possible to access the biological analysis device 18 contained in the package. Such a sheet is advantageously an aluminium sheet which has sealing properties, notably by adding onto the aluminium a polymer layer which enables sealing. Films marketed by the company AMCOR under the reference DD133 may be cited by way of example.

A desiccation means 16 and an analysis device 18 are present inside the cavity 13. The desiccation means 16 serves to absorb any humidity trapped in the cavity 13 when the sheets 12 and 14 are sealed. It is constituted here of a solid polymer material which contains a desiccant. One such material is for example that marketed by the company CSP Technologies™ under the Activ-Polymer® mark. It is furthermore described in document WO-A-00/63288.

The fact that the material constituting the desiccation means 16 is present in this form is essential in the present invention. Indeed, it thus makes it possible to use said desiccation means 16 as a means of perforating the package, such as described infra. To this end, the desiccation means is preferably substantially rectangular parallelepiped in its general shape. Indeed, it appears that this shape permits optimised package opening, notably due to the fact that this opening arrangement is relatively wide, enabling easy access to the analysis device 18.

As far as the biological analysis device 18 is concerned, this may be in the form of a reaction strip. By way of example, such a reaction strip may be a strip bearing antibiotics in the form of a concentration gradient. Such a strip is marketed by the applicant under the Etest® mark.

It should furthermore be noted that if in the embodiment of the article according to the invention, described here in connection with FIGS. 1 to 4A, the device is in the form of a single strip, it may nevertheless certainly be possible to envisage placing several superimposed strips inside the package.

Returning to the first sheet 12, this has a particular shape, as explained supra. This can be clearly seen in FIG. 2. Indeed, it has a left part with reliefs, whereas its right part is relatively flat. With regard to the left part, it should firstly be noted that it has an area 20 with a limited projection. It follows from this that, at this point, the space between the sheets 12 and 14 is relatively limited. This area makes it possible to position the desiccation means 16 very precisely. Indeed, in this area, the end 161 of the desiccation means is sandwiched between the sheets 12 and 14. It is therefore possible to hold the desiccation means in place without using any gluing means whatsoever, and an adhesive in particular.

The left part, in relief, then has two more pronounced bulging areas 21 and 22 separated by a substantially rectilinear and transverse notch 23. This arrangement makes it possible to concentrate the stresses on the notch 23, when the package is folded to open it. The folding forces exerted on the package are shown in the figure by the arrows F1, F2 and F3. The concentration of the forces of action on the notch 23, results in a transverse fold. This is clearly shown in FIGS. 3 and 4A.

Furthermore, the notch 23 has a second function. During the folding of the package such as explained above, the notch 23 which is in contact with the desiccation means 16, acts as a lever aim exerting pressure on said desiccation means. This pressure is passed onto the free end 162 of said desiccation means 16, which then pierces the second sheet 16, thus resulting in the opening of the package.

Figure 3:
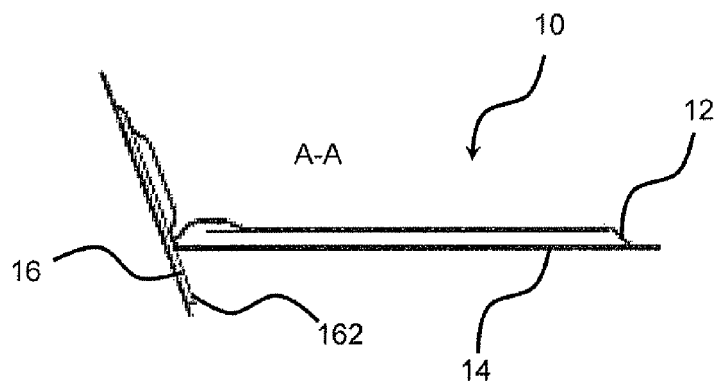
FIG. 3 shows a longitudinal cross-section along axis A-A of the article for biological analysis shown in FIG. 1, after folding and opening of the package.
Figure 4A:
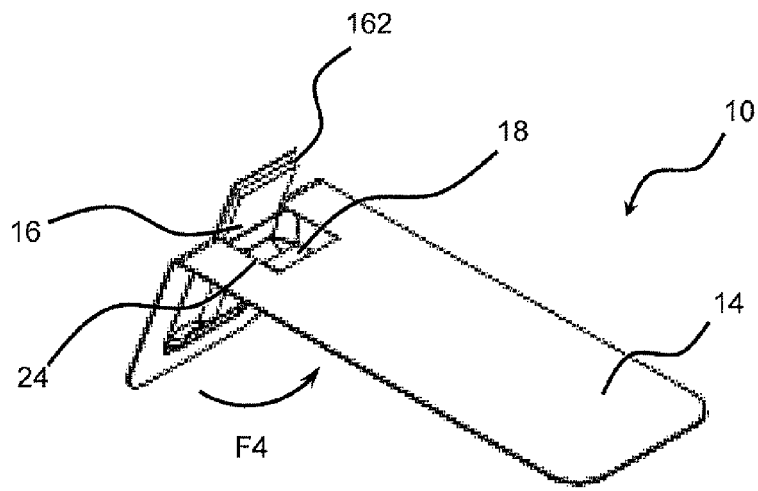
FIG. 4A shows a perspective view of the article for biological analysis according to the invention, after folding and opening of the package.
Figure 4B:
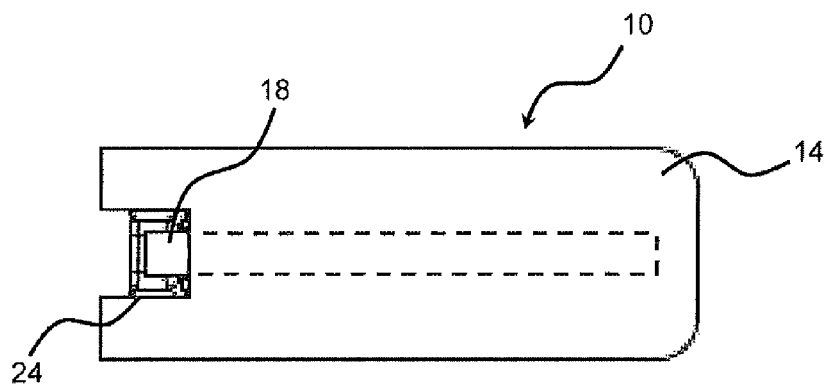
FIG. 4B shows a top view of the article for biological analysis according to the invention, after complete folding.

As can be seen in FIGS. 4A and 4B, in which the article 10 is shown the other way round compared to FIG. 3, the opening as is arranged in the sheet 14 makes the biological analysis device 18 appear and allows the handler handling the article for biological analysis 10 to access said device 18. To do so, he need only fold the article 10 fully back on itself, in accordance with the arrow F4, such that the parts of the sheet 12 on either side of the fold are adjoining. This configuration, shown in FIG. 4B, gives optimised and easy access to the biological analysis device 18, which can then be extracted from the package with the aid of a gripping means, such as tongs. To this end, the bulging area 22 facilitates the extraction of the biological analysis device 18. Indeed, as can be seen in FIGS. 2 and 3, this bulging area 22 substantially frees the space around the free end of the biological analysis device 18, which facilitates access by the gripping means.

The invention claimed is:

1. An article for biological analysis, comprising:
   a first sheet;
   a second sheet, superimposed on said first sheet, said first and second sheets being joined on all of their sides in order to form a sealed package;
   at least one analysis device, placed inside said package; and
   rigid desiccation means, also constituting a means of perforating the first or second sheet of said package, in order to access the analysis device, wherein
   one of said first and second sheets contains a notch which constitutes a preferential folding area; and
   said notch is in direct contact with said rigid desiccation means at least during folding of the package at the preferential folding area.

2. The article according to claim 1, wherein the desiccation means is a solid polymer material containing a desiccant.

3. The article according to claim 1, wherein the desiccation means is substantially rectangular parallelepiped in shape.

4. The article according to claim 1, wherein one of said first and second sheets includes an analysis device gripping area.

5. The article according to claim 1, wherein the biological analysis device is a reaction strip.

6. The article according to the claim 5, wherein the reaction strip bears antibiotics in the form of a concentration gradient.

7. The article according to claim 1, wherein at least one of said first and second sheets comprises an aluminium layer.

8. The article according to claim 1, wherein at least one of said first and second sheets comprises an aluminium-polymer composite laminate.

9. A biological analysis method comprising:
   accessing the analysis device of the article of claim 1.

10. The article according to claim 1, wherein said rigid desiccation means includes a portion configured to pierce one of said first and second sheets, resulting in the opening of the package.

11. The article according to claim 1, wherein said rigid desiccation means is sandwiched between said first and second sheets.

12. The article according to claim 1, wherein said first sheet includes two pronounced bulging areas separated by said notch configured to concentrate stresses on the notch when the package is folded.

13. The article according to claim 1, wherein said notch acts as a lever arm exerting pressure on said rigid desiccation means, thereby causing a free end of said desiccation means to pierce said second sheet and resulting in the opening of the package.

14. An article for biological analysis, comprising:
a first sheet;
a second sheet having sides joined to sides of the first sheet to form a sealed package;
at least one analysis device inside of the sealed package;
a rigid desiccation member within the package that is configured to perforate the first or second sheet of the package in order to provide access to the analysis device; and
a notch on the first or second sheet that constitutes a preferential folding area,
wherein the notch is in direct contact with said rigid desiccation member at least during folding of the package at the preferential folding area.

15. The article according to claim 14, wherein the first or second sheet includes pronounced bulging areas separated by the notch so as to be configured to concentrate stresses on the notch when the package is folded at the preferential folding area.

16. The article according to claim 14, wherein the notch is a substantially transverse notch across the first or second sheet.

17. The article according to claim 14, wherein the rigid desiccation member is sandwiched between and in direct contact with both the first and second sheets.

* * * * *